US00PP10037P

United States Patent [19]

Polys

[11] Patent Number: Plant 10,037

[45] Date of Patent: Sep. 23, 1997

[54] CHRYSANTHEMUM PLANT NAMED 'GOLDEN EL PASO'

[75] Inventor: Susan M. Polys, Salinas, Calif.

[73] Assignee: Yoder Brothers, Inc., Barberton, Ohio

[21] Appl. No.: 605,817

[22] Filed: Feb. 22, 1996

[51] Int. Cl.[6] ..... A01H 5/00

[52] U.S. Cl. ..... Plt./78

[58] Field of Search ..... Plt./78

[56] References Cited

U.S. PATENT DOCUMENTS

P.P. 8,831 7/1994 VandenBerg ..... Plt./79
4,616,099 10/1986 Sparkes ..... 47/58

OTHER PUBLICATIONS

Broertjes, et al., 1980, "A mutant of a mutant of a . . . Irradiation of progressive radiation–induced mutants in a mutation breeding programme with *Chrysanhemum morifolium*", Euphytica, 29:525–530.

Gosling, ed., 1979, "The Chrysanthemum Manual—6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x–rays", Am. Soc. Hort. Sci. Proc., pp. 613–620.

Broertjes, 1966, "Mutation breeding of chrysanthemums", Euphytica 15:156–162.

Dowrick, et al., 1966, "The induction of mutations in chrysanthum using x– and gamma radiation", Euphytica, 15:204–210.

*Primary Examiner*—Howard J. Locker
*Attorney, Agent, or Firm*—Foley & Lardner

[57] ABSTRACT

A Chrysanthemum plant named Golden El Paso particularly characterized by its flat capitulum form; decorative capitulum type; yellow ray floret color; diameter across face of capitulum of 89 to 114 mm when fully opened, when grown as a pinched disbudded pot mum; photoperiodic flowering response of 52 to 59 days after start of short days; plant height, with 15 to 16 long days after sticking unrooted cuttings and with 1 to 2 applications of 2500 ppm B-9 SP ranges from 23 to 28 cm when grown as a pinched pot mum with 4 cuttings in a 15 cm pot; branching pattern is spreading, each plant having 3 to 5 laterals after pinch; and recommended as a disbudded pot mum.

1 Drawing Sheet

The present invention comprises a new and distinct cultivar of Chrysanthemum, botanically known as *Dendranthema grandiflora*, and referred to by the culitivar name Golden El Paso.

Golden El Paso, identified as 4049 (90-747A02), is a product of a mutation induction program. The new cultivar was discovered and selected by inventor Susan M. Polys on Dec. 21, 1992 in a controlled environment in Salinas, Calif. as one flowering plant within a flowering block established as rooted cuttings from stock plants which had been exposed as unrooted cuttings to an X-ray source of 1500 rads in Fort Myers, Fla. on Aug. 6, 1992. The irradiated parent cultivar was the cultivar El Paso, disclosed in U.S. Plant Pat. No. 8,831, and described as a flat decorative disbud pot mum with a light bronze flower color.

The irradiation program resulting in Golden El Paso had as its primary objective the expansion of color ranges of the parent cultivar. The irradiation program comprised irradiation of cuttings of the parent cultivar at irradiation levels of 1500, 1750 and 2000 rads. A total of 721 cuttings harvested from a total of 225 irradiated plants were planted on Oct. 26, 1992. Of these, 10 initial selections were made, which selections were then revegetated and reflowered. Three consecutive flowerings resulted in discarding 9 of the original 10 selections on Aug. 23, 1993. One selection was reselected on Aug. 2, 1993, prior to discarding the original selection. The 1 remaining selection and the 1 reselection were maintained as PIs (Possible Introductions) and further trialed in Salinas, Calif. and Leamington, Ontario, Canada, ultimately resulting in discarding the one original selection on May 31, 1994, and the decision to introduce the one remaining reselection as Golden El Paso.

The first act of asexual reproduction of Golden El Paso was accomplished when vegetative cuttings were taken from the initial selection in March of 1993 in a controlled environment in Salinas, Calif., by technicians working under supervision of Susan M. Polys.

Horticultural examination of controlled flowerings of successive plantings has shown that the unique combination of characteristics as herein disclosed for Golden El Paso are firmly fixed and are retained through successive generations of asexual reproduction.

Golden El Paso has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Leamington, Ontario, Canada, under greenhouse conditions which approximate those generally used in commercial greenhouse practice.

The following traits have been repeatedly observed and are determined to be basic characteristics of Golden El Paso, which, in combination, distinguish this Chrysanthemum as a new and distinct cultivar:

1. Flat capitulum form.
2. Decorative capitulum type.
3. Yellow ray floret color.
4. Diameter across face of capitulum of 89 to 114 mm when fully opened, when grown as a pinched disbudded pot mum.
5. Photoperiodic flowering response of 52 to 59 days after start of short days.

6. Plant height, with 15 to 16 long days after sticking unrooted cuttings and with 1 to 2 applications of 2500 ppm B-9 SP ranges from 23 to 28 cm when grown as a pinched pot mum with 4 cuttings in a 15 cm pot.

7. Branching pattern is spreading, each plant having 3 to 5 laterals after pinch.

8. Recommended as a disbudded pot mum.

The accompanying photographic drawing is a side view of Golden El Paso, grown as a disbudded pot mum with 4 cuttings in a 15 cm pot, with the colors being as nearly true as possible with illustrations of this type.

Of the commercial cultivars known to the inventor, the most similar in comparison to Golden El Paso is the parent cultivar El Paso. All traits of Golden El Paso are similar to those of El Paso, except for the ray floret color. The ray floret color of Golden El Paso is yellow (R.H.S. 3A), while the ray floret color of El Paso is yellow-orange (R.H.S. 22B to 22C).

In the following description color references are made to The Royal Horticultural Society Colour Chart. The color values were determined on plant material grown as a pinched pot mum with 4 cuttings in a 15 cm pot in Salinas, Calif. on May 22, 1995.

Classification:

*Botanical.*—*Dendranthema grandiflora* cv Golden El Paso.

*Commercial.*—Flat decorative disbud pot mum.

INFLORESCENCE

A. Capitulum:

*Form.*—Flat.

*Type.*—Decorative.

*Diameter across face.*—89 to 114 mm when fully opened.

B. Corolla of ray florets:

*Color (general tonality from a distance of three meters)*.—Yellow.

*Color (upper surface).*—3A.

*Color (under surface).*—3C.

*Shape.*—Straight, ribbed, some spoons in outer rows of ray florets; pointed petal tips.

C. Corolla of disc florets:

*Color (mature).*—7B.

*Color (immature).*—144A to 144B.

D. Reproductive organs:

*Androecium.*—Present on disc florets only; no pollen.

*Gynoecium.*—Present on both ray and disc florets.

PLANT

A. General appearance:

*Height.*—23 to 28 cm when grown as a pinched pot mum with 15 to 16 long days after sticking unrooted cuttings prior to start of short days and with 1 to 2 applications of 2500 ppm B-9 SP.

*Branching pattern.*—Spreading, with 3 to 5 laterals after pinch.

B. Foliage:

*Color (upper surface).*—147A.

*Color (under surface).*—147B.

*Shape.*—Lobed and slightly serrated.

What is claimed is:

1. A new and distinct Chrysanthemum plant named Golden El Paso, as described and illustrated.

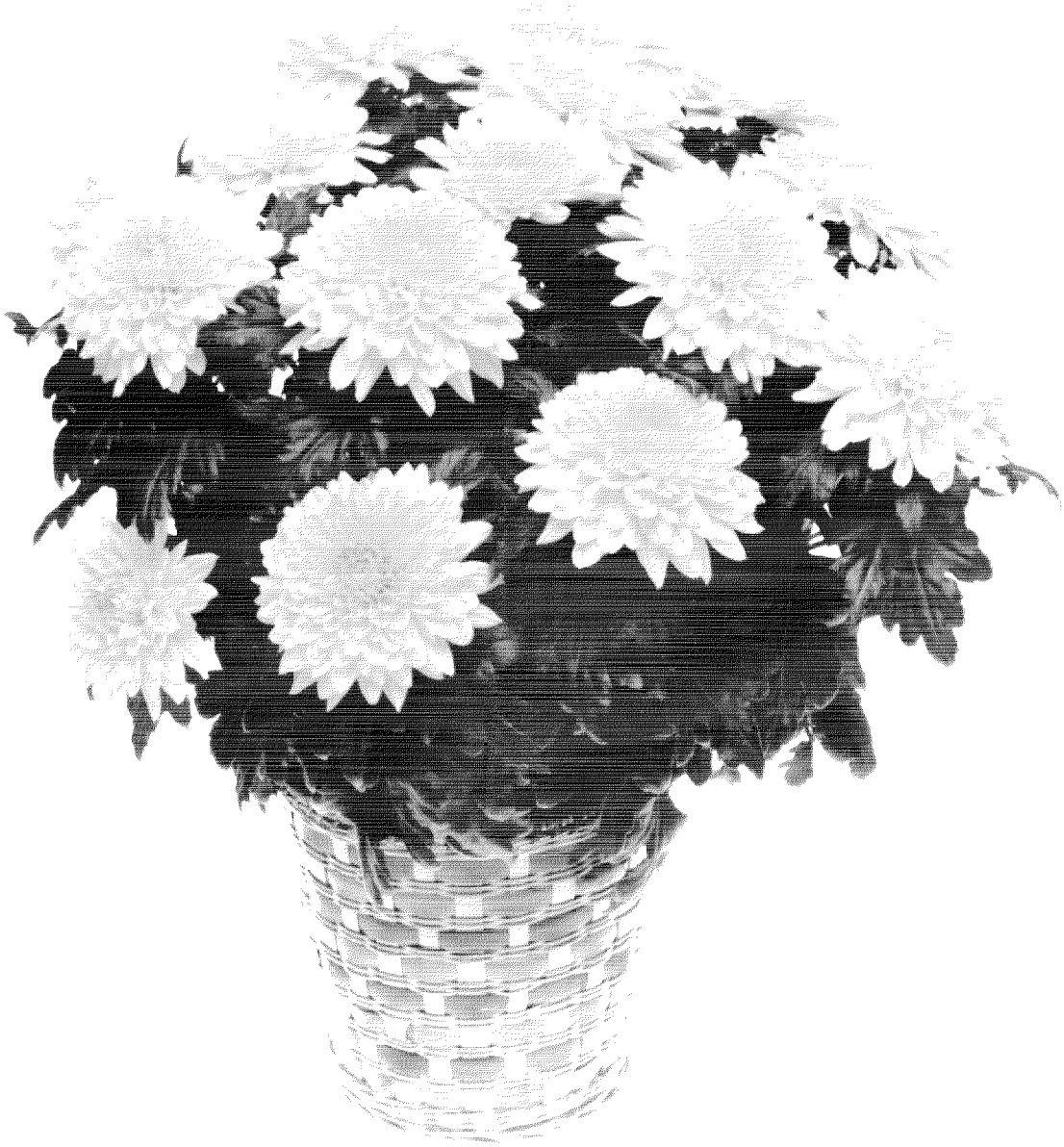

* * * * *